United States Patent [19]

Ocampo et al.

[11] 4,119,497
[45] Oct. 10, 1978

[54] PROCESS FOR THE PURIFICATION OF ACETONITRILE

[75] Inventors: Felipe Ocampo; Francisco Meza; Francisco Aguirre, all of Mexico City, Mexico

[73] Assignee: Instituto Mexicano del Petroleo, Mexico City, Mexico

[21] Appl. No.: 731,633

[22] Filed: Oct. 12, 1976

[30] Foreign Application Priority Data

Dec. 1, 1975 [MX] Mexico .................................. 162235

[51] Int. Cl.$^2$ ...................... B01D 3/36; C07C 121/18
[52] U.S. Cl. ........................................ 203/29; 203/37; 203/38; 203/69; 203/71; 260/465.1
[58] Field of Search ....................... 203/29, 33, 36, 37, 203/38, 81, 71, 69, 95–96, DIG. 3, 60; 260/465.1, 465.3, 465.9

[56] References Cited

U.S. PATENT DOCUMENTS

| 2,305,106 | 12/1942 | Pratt | 260/465.1 |
| 2,616,838 | 11/1952 | Williams | 260/465.1 |
| 2,807,573 | 9/1957 | Robertson | 203/33 |
| 2,827,423 | 3/1958 | Carpenter | 203/37 |
| 3,201,451 | 8/1965 | Idol et al. | 203/29 |
| 3,210,399 | 10/1965 | Krzemicki | 260/465.1 |
| 3,247,237 | 4/1966 | Hagemeyer | 260/465.1 |
| 3,442,771 | 5/1969 | Jordan et al. | 203/37 |
| 3,462,477 | 8/1969 | Caporali et al. | 203/37 |
| 3,896,007 | 7/1975 | Rescalli et al. | 203/33 |

*Primary Examiner*—Wilbur L. Bascomb, Jr.
*Attorney, Agent, or Firm*—Finnegan, Henderson, Farabow & Garrett

[57] ABSTRACT

The present invention refers to a process for the purification of acetonitrile from crude acetonitrile or mixtures containing the same, which comprises the following operations:
(a) transformation of hydrogen cyanide and acrylonitrile into compounds of higher molecular weight,
(b) removal of most of the water in an azeotropic distillation column, and
(c) separation of acetonitrile from the compounds of higher molecular weight and residual water in rectifying columns.

6 Claims, 1 Drawing Figure

FLOW DIAGRAM

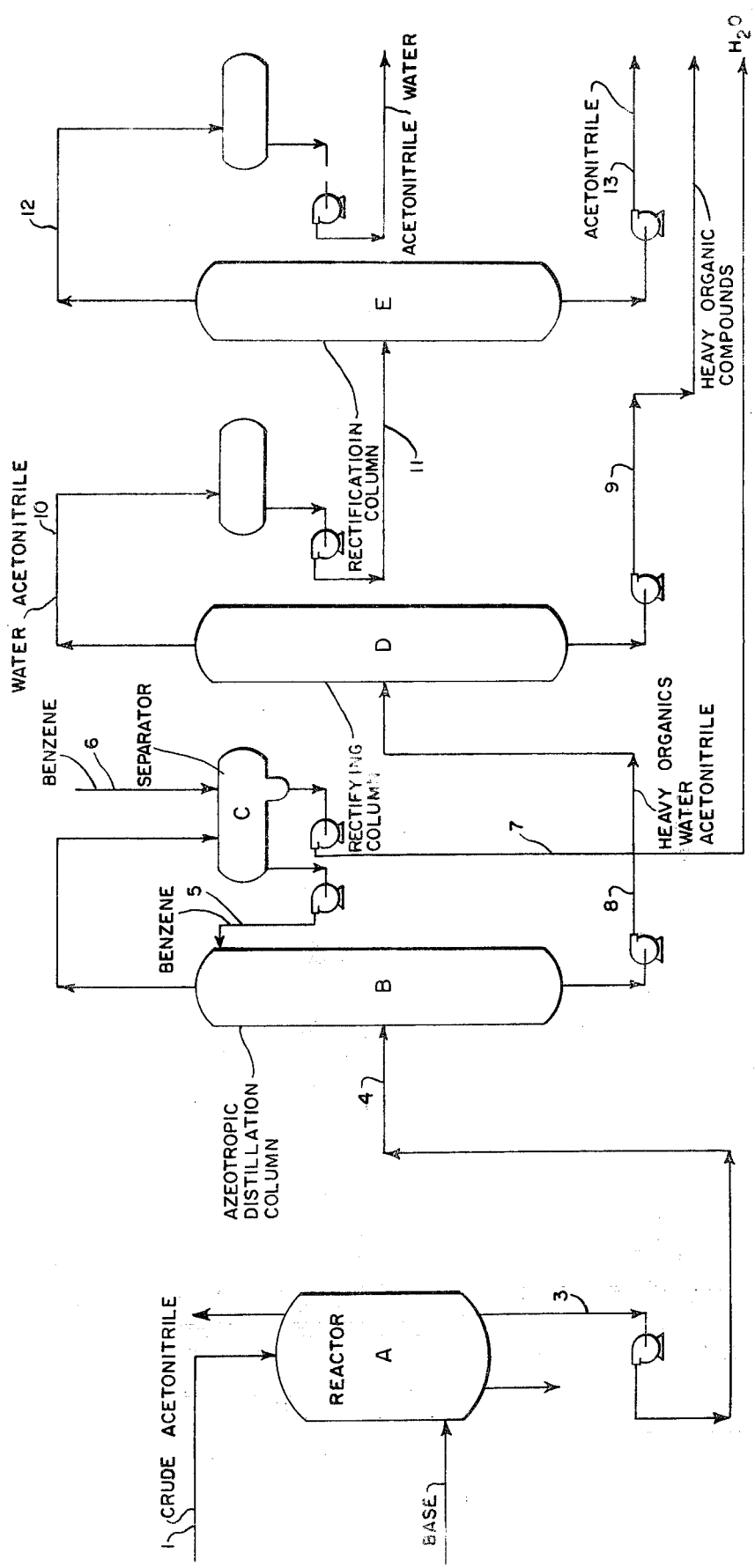

PROCESS FOR THE PURIFICATION OF ACETONITRILE

BACKGROUND OF THE INVENTION

Mixtures that contain acetonitrile and other compounds considered as impurities are commonly denominated "crude acetonitrile" and they are originated in the production process of acrylonitrile.

Due to both economic and technical factors, a certain time ago the recovery of acetonitrile from mixtures containing the same, was not considered feasible. However, the present changes in these factors at world level have given rise to the need to carry out various investigations for the development of processes to obtain and purify acetonitrile.

The processes for purifying acetonitrile have as their object to eliminate mainly: acrylonitrile, hydrogen cyanide and water, which are generally the impurities that accompany the acetonitrile. Nevertheless, other impurities may also be present such as 3,3'iminodipropionitrile and epoxides, in insignificant amounts. Prior to the present invention, the methods used have included contacting the crude acetonitrile with chemicals and effecting thereafter operations to separate purified acetonitrile from the remaining compounds.

For examle, in the U.S. Pat. No. 3,322,814, the purification of crude acetonitrile is described, putting the same in contact with $KMnO_4$, and performing later on a filtration to obtain the purified acetonitrile.

In the U.S. Pat. No. 3,328,458 a process is claimed for purifying a mixture of acetonitrile, with $H_2O$, and HCN, which process comprises stirring the crude acetonitrile and adding thereto a certain amount of $CaCl_2$ and copper acetate, continuing the stirring for 3 hours at a temperature of 25° C., allowing the mixture to stand so as to be able to separate an acetonitrile-rich part and an aqueous part, and then finally adding to the organic layer $Ca(OH)_2$ and HCN, to be able to utilize the said mixture in further industrial applications.

In the French Pat. No. 1,431,919, a process is disclosed for purifying acetonitrile admixed with 4.8% acrylonitrile and 17.3% water, to which mixture 0.023 mols of NaOH is added per kg of mixture and methanol is added in a molar ratio of 4:1 with regards to acrylonitrile. Then the mixture is refluxed for 90 minutes, reducing the acrylonitrile contents up to 0.015%, and thus obtaining the acetonitrile by neutralization of the mixture and by extraction thereof.

In the U.S. Pat. No. 3,451,899, a process for purifying acetonitrile is claimed by means of azeotropic distillation and neutralization, which comprises feeding crude acetonitrile to a distilling column, discharging thereof through the upper part a stream which contains about 100 ppm of HCN, which is treated with 0.25 N, NaOH and 0.25 N, $FeSO_4$ solutions, and which is contacted thereafter with benzene so as to form an aqueous layer and an organic layer, which, after separation, is washed with water.

The relatively dry acetonitrile is obtained at the bottom of the column and then is distilled in a second column.

There exist other processes for the purification of crude acetonitrile which employ extractive distillation and rectifying operations. However, in these processes problems arise from the formation of azeotropic mixtures such as water-acetonitrile, water-acrylonitrile, benzene-acrylonitrile, which are separated with difficulty.

The previous processes present a series of inconveniences which render them impractical, since they require operations that last for a long time and which are, therefore, expensive.

Said processes generally use chemicals which are difficult to handle, especially on the industrial scale required for purification operations, making their use prohibitively expensive.

Due to the purification processes as mentioned above generally involving separating operations such as decantation and settling, they are batchwise processes which present great technical and economic inconveniences compared to the continuous type of processes.

Most processes known up to this moment only eliminate some of the impurities which are generally present in crude acetonitrile.

In general terms one may say that the present methods of purification result in the formation of undesired by-products, which present problems concerning their elimination or possible reutilization.

OBJECT OF THE INVENTION

So, therefore, it is an object of the present invention to provide a continuous process for purifying at industrial scale crude acetonitrile, which does not present the inconveniences of the processes as mentioned previously.

Another object of the present invention consists of supplying a method for the elimination of the impurities as contained in crude acetonitrile.

Another of the objects of the present invention resides in the supply of an economical method, which at the same time has a high level of safety, for eliminating highly toxic compounds such as HCN and acrylonitrile.

Finally, another object of the present invention is providing a method which utilizes moderate operative conditions which allow the use of conventional equipment and which achieves a 100% purity of acetonitrile.

DETAILED DESCRIPTION OF THE INVENTION

In accordance with the works carried out by the applicant, it has been found that the transformation in an initial stage of the impurities, mainly constituted by hydrogen cyanide and acrylonitrile, to compounds which may be eliminated with greater ease in later stages, gives as a result a surprisingly efficient method for the purification of crude acetonitrile.

The transformation of hydrogen cyanide and of acrylonitrile is performed by means of a base which may have an organic or inorganic nature. Examples of bases that may be used are alkali metal hydroxides, such as sodium hydroxide, ammonium hydroxide, ammonia, and aliphatic amines, such as those containing 5 to 15 carbon atoms in the alkyl group, for example dodecylamine. The transformation may proceed in accordance with the following chemical reactions:

Reaction with: NaOH

$$HCN + 2H_2O \xrightarrow{NaOH} H-COONH_4 \quad (1)$$

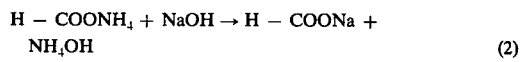

$$H-COONH_4 + NaOH \rightarrow H-COONa + NH_4OH \quad (2)$$

Reaction with: $NH_4OH$

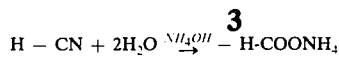  (3)

Reaction with: $NH_3$

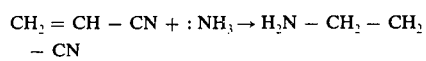  (4)

In accordance with the previous reaction, it occurs now that it is possible to transform hydrogen cyanide and acrylonitrile, respectively, into compounds having a major molecular weight, which compounds, as has already been said, may be eliminated easily in subsequent stages, which comprise:
(a) Extractive distillation
(b) Rectifying of acetonitrile The above may be achieved due to the fact that both the hydrogen cyanide and the acrylonitrile are transformed into compounds of a higher boiling temperature, which impedes the formation of azeotropes like water/acrylonitrile, and benzene/acrylonitrile, which are difficult to separate.

DETAILED DESCRIPTION OF THE DRAWINGS

The method of the invention is explained hereinafter with full detail, for which purpose use is made of a flow diagram (FIGURE), which shows one of the possible alternatives which may be followed within the outlines of the present invention.

Through line 1, crude acetonitrile is fed to a reactor "A", making use of line 2, the organic or inorganic base is introduced into reactor "A", wherein at an appropriate temperature and pressure, the transformation is effected of the hydrogen cyanide and acrylonitrile into compounds having a higher boiling point; through the bottom of the reactor, through line 3, the mixture of the reaction is circulated and the same is fed at 4 into an azeotropic distillation column "B", into which also benzene is fed at 5, which comes from a separator "C", into which in turn benzene is introduced at 6; at the bottom of the separator "C", at 7, water is eliminated from the system; at the bottom of the azeotropic distillation column, at 8, a mixture is discharged which is formed by acetonitrile, residual water and heavy organic compounds, which is fed through line 8 to a rectifying column "D". At the lower part thereof, at 9, the separation from the system is effected of the heavy organic compounds, and at the top of the column at 10, a mixture is obtained of acetonitrile and residual water, which is fed at 11 into a rectification column "E"; in the top thereof, 12, an azeotropic mixture is obtained of acetonitrile-water, and at the bottom, in 13, the purified acetonitrile is obtained.

The reactions which are carried out for the transformation of HCN and acrylonitrile in the first stage of the process according to the present invention, refers to the treatment of mixtures of crude acetonitrile which present various compositions, and particularly to mixtures obtained as a by-product of the manufacturing process for acrylonitrile, which may be comprised within the range of concentrations as stated hereunder:

| COMPONENT | WEIGHT % |
|---|---|
| $CH_3$ — CN | 52 – 70 |
| HCN | 2.0 – 4.0 |
| $CH_2$ = CH — CN | 0.30 – 3.0 |
| other nitriles | 0.50 – 2.0 |
| other organic compounds | 0.10 – 2.0 |

-continued

| COMPONENT | WEIGHT % |
|---|---|
| water | 30 – 60.0 |

With the purpose to illustrate in a clearer manner the present invention, hereinafter some examples are described which support the contents of the present application, but which, of course, do not limit the scope of the invention.

In the following examples, the elimination of HCN from the crude acetonitrile is effected with the use as reactants of sodium hydroxide or ammonium hydroxide, considering that the hydrogen cyanide, in reaction with water, and in the presence of a base, is converted into other compounds having a higher molecular weight, according to the reactions (1) and (3), as mentioned above.

The experimentation has as its base, a sample of crude acetonitrile, with 2 to 10 ppm of hydrogen cyanide and a pH of 7.86, utilizing a sodium hydroxide solution (20 weight percent) or ammonium hydroxide with a concentration of $NH_3$ from 27 to 29 weight %.

In the examples A and B, the manner is shown wherein the various concentrations of NaOH or $NH_4OH$ exercise their influence, in their conditions or qualities as used for the elimination of HCN from the first stage of the reaction, i.e. in reactor "A".

EXAMPLE "A"

For a mixture of crude acetonitrile, which contains from 2 to 10 ppm of HCN, with a pH from 7 to 12.5, different runs were carried out so as to eliminate HCN by means of the addition of a solution of sodium hydroxide (20%). In a first run a mixture of crude acetonitrile is used which contains 2 ppm of HCN, and the said mixture is reacted with 0.00369 gal of NaOH for each 26.42 gal of crude acetonitrile, and thus a conversion of HCN is obtained of 100 percent.

In a second run, a mixture is used of crude acetonitrile which contains 10 ppm of HCN, and the same is reacted with 0.0188 gal of NaOH for each 26.42 gal of crude acetonitrile, being obtained a conversion of HCN of 100 percent.

EXAMPLE "B"

For a mixture of crude acetonitrile which contains from 2 to 10 ppm of HCN, with a 7.8 to 10.5, different runs were performed so as to eliminate HCN by means of the addition of ammonium hydroxide.

In a first run, a mixture is used of acetonitrile containing 2 ppm of HCN, and the same mixture is reacted with 0.0073 gal of $NH_4OH$ for each 26.42 gal of crude acetonitrile, being thus obtained a conversion of HCN equal to 100 percent.

In a second run, a mixture is used of crude acetonitrile containing 3.5 ppm of HCN, and at a pH of 10.2 the said mixture is reacted with 0.0132 gal of $NH_4OH$ for each 26.42 gal of crude acetonitrile, being thus obtained a conversion of HCN equal to 100 percent.

In a third run, a mixture is used of crude acetonitrile containing 10 ppm of HCN, then the said mixture is reacted with 0.0376 gal of $NH_4OH$ for each 26.42 gal of crude acetonitrile, being thus obtained a conversion of HCN equal to 100 percent.

The examples 1 to 14, which are stated hereunder, provide the results of the acrylonitrile conversion, when different temperatures, reaction times and molar ratios of ammonia/acrylonitrile are used, during the first step of the purification process of the mixture of crude acetonitrile.

EXAMPLE 1

In an adequate reactor, a stream of ammonia is reacted with acrylonitrile which is contained in a mixture of crude acetonitrile, in a molar ratio of ammonia/acrylonitrile of 0.5:1, for a reaction time of about 3 hours and 42 minutes, and at a temperature of 176° F., being thus obtained a conversion of acrylonitrile of 100 percent.

EXAMPLE 2

In the same manner as explained in Example 1, ammonia is reacted with acrylonitrile contained in crude acetonitrile in a molar relation of ammonia/acrylonitrile of 0.5:1, for a reaction time of approximately 5 hours and 35 minutes, at a temperature of 158° F., being thus obtained a conversion of acrylonitrile of 100 percent.

EXAMPLE 3

In accordance with Example 1, ammonia is reacted with acrylonitrile, contained in crude acetonitrile, in a molar ratio of ammonia/acrylonitrile of 1.5:1, for a reaction time of approximately 1 hour and 20 minutes, at a temperature of about 176° F., being thus obtained a yield of conversion of acrylonitrile of 100 percent.

EXAMPLE 4

Operating in the same manner as has been described for Example 3, ammonia is contacted with acrylonitrile contained in crude acetonitrile in a molar ratio of ammonia/acrylonitrile of 1.5:1 for a reaction time of 1 hour and 32 minutes, at a temperature of about 158° F., being a total conversion obtained of acrylonitrile into products having a higher boiling point.

EXAMPLE 5

In accordance with Examples 3 and 4, ammonia is reacted with acrylonitrile, contained in crude acetonitrile in a molar ratio of ammonia/acrylonitrile of 1.5:1, for a reaction time of approximately 5 hours and 45 minutes, at a temperature of 122° F., being a conversion of acrylonitrile obtained of 100 percent.

EXAMPLE 6

In accordance with the Examples 3 to 5, ammonia is reacted with acrylonitrile contained in crude acetonitrile, in a molar ratio of ammonia/acrylonitrile of 1.5:1, for a reaction time of approximately 5 hours and 20 minutes, at a temperature of 104° F., being obtained a conversion of acrylonitrile of 100 percent.

EXAMPLE 7

In accordance with the matter as decribed for example 1, ammonia is reacted with acrylonitrile contained in crude acetonitrile, in a molar ratio of ammonia/acrylonitrile of 3.5:1, in a reaction time of approximately 28 minutes, and at a temperature of 176° F., being obtained a conversion of acrylonitrile of 100 percent.

EXAMPLE 8

Following the process of Example 7, ammonia is reacted with acrylonitrile contained in crude acetonitrile, in a molar ratio of ammonia/acrylonitrile of 3.5:1, for a reaction time of about 58 minutes, and heating at a temperature of 122° F., being obtained a conversion of acrylonitrile of 100 percent.

EXAMPLE 9

In accordance with Example 8, ammonia is reacted with acrylonitrile contained in crude acetonitrile, in a molar ratio of ammonia/acrylonitrile of 3.5 : 1, for a reaction time of approximately 1 hour and 55 minutes, at a temperature of 104° F., being obtained a conversion of acrylonitrile of 100 percent.

EXAMPLE 10

In accordance with the technique as explained with regard to example 1, ammonia is reacted with acrylonitrile contained in crude acetonitrile, in a molar ratio of ammonia/acrylonitrile of 5.3:1, for a time of 1 hour, and at a temperature of about 68° F., being thus obtained a conversion of acrylonitrile of practically 100 percent.

EXAMPLE 11

In accordance with example 1, ammonia is reacted with acrylonitrile contained in crude acetonitrile in a molar ratio of ammonia/acrylonitrile of 6:1, for a reaction time of about 1 hour and at a temperature of 50° F., being thus obtained a conversion of acrylonitrile of practically 100 percent.

EXAMPLE 12

In accordance with the procedure of Example 1, ammonia is reacted with acrylonitrile contained in crude acetonitrile in a molar ratio of ammonia/acrylonitrile of 7.8:1, for a reaction time of approximately 20 minutes and at a temperature of 158° F., being thus obtained a conversion of practically 100 percent of acrylonitrile into products having a higher boiling point.

EXAMPLE 13

According to the procedure of Example 1, ammonia is reacted with acrylonitrile contained in crude acetonitrile in a molar ratio of ammonia/acrylonitrile of 12:1, in a reaction time of about 30 minutes and at a temperature of 86° F., being there obtained a conversion of practically 100 percent of acrylonitrile.

EXAMPLE 14

In accordance with the procedure of Example 1, ammonia is reacted with acrylonitrile contained in crude acetonitrile in a molar ratio of ammonia/acrylonitrile of 8.8:1, for a reaction time of 40 minutes, at a temperature of 68° F., being there obtained a conversion of acrylonitrile of 100 percent.

In the examples 15 and 16, which are described hereunder, an aliphatic amine was used; this is an organic base, instead of ammonia.

EXAMPLE 15

In an adequate reactor, dodecylamine is reacted with acrylonitrile contained in crude acetonitrile in a molar ratio of dodecylamine/acrylonitrile of 2:1, for a reaction time of about 1 hour and 30 minutes, and at a temperature of 158° F., being there obtained a conversion of acrylonitrile of 94 percent.

EXAMPLE 16

In accordance with the procedure of Example 15, a dodecylamine compound is reacted with acrylonitrile, contained in crude acetonitrile, in a molar ratio of dodecylamine/acrylonitrile of 1:1, for a reaction time of about 1 hour and 30 minutes, at a temperature of 158° F., being there obtained a conversion of acrylonitrile of 90 percent.

In the followng Examples I and II, the efficacy of the process is demonstrated, so as to eliminate the contaminants of the mixture of crude acetonitrile.

EXAMPLE I

Into a reactor "A", a mixture is fed to crude acetonitrile which presents the following composition:

| Hydrogen Cyanide | 8 ppm |
|---|---|
| Acetonitrile | 43.7 mol % |
| Acrylonitrile | 7.8 mol % |
| Others | 1.73 mol % |
| Water | 46.82 mol % |

With a consumption of 7.907 mol lb/hr of ammonia, the reaction was carried out at an approximate temperature of 132.8° F. and at a pressure of 14.7 pound/inch$^2$, and thus a mixture was obtained, presenting the following composition:

|  | Mol % |
|---|---|
| Acetonitrile | 43.70 |
| Others | 9.46 |
| Water | 46.84 |
| HCN | 0 |
| Acrylonitrile | 0 |

The temperature of the resulting mixture is elevated to 168.8° F. and the same is fed to an azeotropic distilling column "B"; to this same column, simultaneously, a benzene stream is fed at a temperature of about 104° F. and at a pressure of 14.7 pound/inch$^2$. In this azeotropic distillation column, at the top, a separation is effected of most of the water and NH$_3$ from the mixture. The charge or load of the bottom thereof, is fed to a rectification column "D", and this charge presents the following composition:

|  | Mol Per cent |
|---|---|
| Acetonitrile | 80.608 |
| Others | 15.561 |
| Water | 3.800 |

At an approximate temperature of 191.3° F. and at a pressure of 14.7 pounds/inch$^2$, at the bottom of this column, the heavy organic compounds are eliminated and at the roof or dome 4.56 mol % of residual water is eliminated as well as 95.44% mol % of acetonitrile, at a temperature of 168.8° F., and a pressure of 14.7 pound/inch$^2$. This final mixture is fed to a rectification column "E", at a temperature of about 179.6° F. and at a pressure of 14.7 pound/inch$^2$, wherein through the dome an azeotropic mixture of acetonitrile-water is separated and through the bottom 14.8874 lb mol/hr of purified acetonitrile is obtained, having the latter excellent properties, the specifications of which fulfill those of commercial acetonitrile.

EXAMPLE II

Following the same technique as described for Example I, to a reactor "A" a mixture of crude acetonitrile is fed with the following composition:

|  | Mol Per cent |
|---|---|
| Acetonitrile | 42.350 |
| Acrylonitrile | 0.457 |
| Propionitrile | 0.153 |
| Other nitriles | 0.488 |
| Water | 54.122 |
| Hydrogen Cyanide | 2.430 | with a consumption of 2.561 mol lb/hr, of ammonia the reaction being preformed at a temperature of 132.8° F. and at a pressure of 14.7 pound/inch$^2$, being there obtained a mixture of acetonitrile in the reactor "A", having the following composition:

|  | Mol Per cent |
|---|---|
| Acetonitrile | 42.350 |
| Others | 3.408 |
| Water | 49.242 |
| Acrylonitrile | 0 |
| HCN | 0 |

The said mixture is fed, at a temperature of 168.8° F., and at a pressure of 14.7 pound/inch$^2$, into a column of azeotropic distillation "B", and also benzene is fed at a temperature of about 104° F. so as to eliminate by refluxing, the greater part of the water and NH$_3$ from the mixture.

The bottom charge of column "B" is sent to a rectification column "D", in such a manner that the said mixture presents the following composition:

|  | Mol Per cent |
|---|---|
| Water | 4.950 |
| Acetonitrile | 88.980 |
| Others | 6.062 |

The feed temperature of the mixture is 185.5° F., and through the bottom of the rectification column "D" the heavy organic compounds are eliminated, at a temperature of about 344.3° F., and at a pressure of 14.7 pound/inch$^2$. Through the top of the column, a mixture is separated of 5.270 mol percent of residual water and 94.73 mol percent of acetonitrile at a temperature of 179.6° F. approximately.

Finally, this mixture is fed to a rectification column "E", wherein at the top an azeotrope of acetonitrile-water is separated at a temperature of about 168.8° F. and through the bottom an amount of 14.8874 lb mol/hr of pure acetonitrile is obtained, at an approximate temperature of 179.6° F.

Concluding, one may deduce that the efficiency of the method to purify crude acetonitrile, is remarkably superior with regard to related processes, since in accordance with the values as indicated in the examples "A" and "B", it is demonstrated that the elimination of HCN by means of different concentrations of NaOH or NH$_4$OH is practically total.

In the same manner, the transformation of acrylonitrile into compounds of a higher molecular weight, so as to separate them in an easier way, is practically total, using molar ratios of ammonia and acrylonitrile or aliphatic amines with regard to acrylonitrile and time intervals as those mentioned in the present invention.

Furthermore, the transformation of acrylonitrile into a compound of a higher boiling point, avoids the formation of the azeotropes acrylonitrile/water and acrylonitrile/benzene, and for this reason the process of the present invention is developed in a minor number of stages, and a product may be obtained of a high degree of purity, with the specifications of commercial acetonitrile.

We claim:

1. A process for the purification of crude acetonitrile consisting essentially of:
   (a) feeding said crude acetonitrile, comprising acetonitrile, hydrogen cyanide, acrylonitrile, and water, to a reactor:
   (b) feeding a stream comprising a base selected from the group consisting of alkali metal and ammonium hydroxides, ammonia, and aliphatic amines to said reactor;
   (c) reacting said crude acetonitrile and said base in said reactor at a temperature between 50° F. and 212° F. and at least atmospheric pressure to form a reaction mixture in which said hydrogen cyanide and said acrylonitrile are transformed into compounds of higher molecular weight;
   (d) passing said reaction mixture to an azeotropic distillation column, removing most of said water from said column in an upper stream and removing a bottom stream from said column comprising residual water, said compounds of higher molecular weight, and said acetonitrile;
   (e) passing said bottom stream to a first rectifying column, removing from said first rectifying column a bottom stream comprising said compounds of higher molecular weight, and removing from said first rectifying column an upper stream comprising water and acetonitrile; and
   (f) passing said upper stream from said first rectifying column to a second rectifying column, removing from said second rectifying column a bottom stream of substantially pure acetonitrile, and removing from said second rectifying column an upper stream comprising said residual water and acetonitrile.

2. The process according to claim 1, wherein the reaction time is between 10 minutes and 5 hours, and the molar ratio of said base to acrylonitrile present in said crude acetonitrile is within the range of 0.5/1 to 15/1.

3. The process according to claim 1, wherein said crude acetonitrile is a by-product from an acrylonitrile manufacturing plant.

4. The process according to claim 1, wherein said base is an aliphatic amine present in a molar ratio of aliphatic amine/acrylonitrile of 1:1 to 5:1, and the reaction time is from 0.5 to 5 hours.

5. The process according to claim 14, wherein said aliphatic amine contains from 5 to 15 carbon atoms in the alkyl group.

6. The process of claim 1, wherein said base is ammonia.

* * * * *

UNITED STATES PATENT AND TRADEMARK OFFICE
CERTIFICATE OF CORRECTION

PATENT NO. :  4,119,497
DATED      :  October 10, 1978
INVENTOR(S) :  Felipe Ocampo; Francisco Meza; & Francisco Aguirre It is certified that error appears in the above-identified patent and that said Letters Patent are hereby corrected as shown below:

Column 10, line 23, "14" should read --4--.

Signed and Sealed this

Sixth Day of February 1979

[SEAL]

Attest:

RUTH C. MASON
*Attesting Officer*

DONALD W. BANNER
*Commissioner of Patents and Trademarks*